US00PP18060P2

(12) United States Plant Patent
Lim et al.

(10) Patent No.: US PP18,060 P2
(45) Date of Patent: Sep. 18, 2007

(54) SHRUB ROSE PLANT NAMED 'BAITOWN'

(50) Latin Name: *Rosa hybrida*
Varietal Denomination: BAItown

(75) Inventors: Peter P. Lim, McMinnville, OR (US); Martin Nemko, Oakland, CA (US)

(73) Assignee: Bailey Nurseries, Inc., Newport, MN (US)

( * ) Notice: Subject to any disclaimer, the term of this patent is extended or adjusted under 35 U.S.C. 154(b) by 0 days.

(21) Appl. No.: 11/408,312

(22) Filed: Apr. 21, 2006

(51) Int. Cl.
*A01H 5/00* (2006.01)

(52) U.S. Cl. ..... Plt./102

(58) Field of Classification Search ..... Plt./102, Plt./108
See application file for complete search history.

*Primary Examiner*—Kent Bell
*Assistant Examiner*—Annette H Para
(74) *Attorney, Agent, or Firm*—Penny J. Aguirre

(57) ABSTRACT

A new cultivar of shrub rose, *Rosa* 'BAItown', characterized by its everblooming habit with abundant clusters of double, red-purple, hybrid tea-shaped flowers. The foliage is dense, dark green, glossy, and resistant to rose blackspot and powdery mildew. The even spreading to mounded plant habit is well suited for container and landscape plantings. The new variety is readily propagated on its own roots and hardy in U.S.D.A. Zones 4 to 9.

2 Drawing Sheets

Botanical classification: *Rosa hybrida.*
Variety denomination: 'BAItown'.

BACKGROUND OF THE INVENTION

The present invention relates to a new and distinct cultivar of *Rosa hybrida.* The new cultivar will be referred to hereafter by its cultivar name, 'BAItown'. 'BAItown' is a shrub rose suitable for landscape and container plantings.

The new cultivar of shrub rose is a selection from a controlled breeding program conducted by the inventors in Yamhill, Oreg. with a focus to create cultivars of roses with greater winter hardiness and improvements in disease resistance combined with good flower quality.

The new variety of shrub rose, 'BAItown', designated as seedling No 95K104, was selected among seedlings derived from a cross made in Yamhill, Oreg. in 1995 between the female parent, 'KORnuma' (not patented) and the male parent, 'JACcasp' (U.S. Plant Pat. No. 8,719). 'BAItown' was selected as unique and budded onto understock in 1996 and reselected by the inventors for its distinct characteristics in 1999.

The new cultivar has been asexually propagated by budding on an understock of 'Dr. Huey' (not patented) and by rooting of softwood cuttings. Asexual propagation in Yamhill, Oreg. , St. Paul, Minn., and Litchfield, Ariz. by these techniques have determined that the characteristics of this cultivar are stable and are reproduced true to type in successive generations.

SUMMARY OF THE INVENTION

The following traits have been repeatedly observed and represent the characteristics of the new rose as observed for a period of four years in Yamhill, Oreg. and St. Paul, Minn. These attributes in combination distinguish 'BAItown' as a unique cultivar of shrub rose.

1. 'BAItown' is densely foliated with a compact, spreading to mounding plant habit.

2. 'BAItown' exhibits dark green, glossy foliage.
3. 'BAItown' is everblooming and blooms continuously throughout the growing season with abundant clusters of red-purple, double, hybrid tea-shaped flowers.
4. 'BAItown' has shown excellent resistance to rose blackspot (*Diplocarpon rosae*) and powdery mildew (*Sphaerotheca pannosa* var. *rosa.*).
5. 'BAItown' is hardy in U.S.D.A. Zones 4 to 9.
6. 'BAItown' is a vigorous grower and readily propagated by rooting of softwood cuttings.

The new cultivar of shrub rose can be readily distinguished from its parents and other cultivars. The female parent, 'KORnuma', a Floribunda, has darker red flowers, lighter colored foliage, and an upright growth habit. The male parent, 'JACcasp', a Miniature Rose, has pink and cream colored flowers, a rounded habit, and is shorter in height. The cultivars 'John Franklin' (not patented) and 'George Vancouver' (U.S. Plant Pat. No. 10,009) are the closest comparison shrub roses. They are both similar to 'BAItown' in having double red flowers, however they are both recurrent bloomers rather than everblooming, have smaller flowers, lighter green foliage, and exhibit more upright plant habits.

BRIEF DESCRIPTION OF THE DRAWING

The accompanying colored photographs illustrate the overall appearance and distinct characteristics of the new shrub rose, 'BAItown', as grown outdoors in trial blocks and containers in St. Paul, Minn. and Yamhill, Oreg. The photographs were taken of two to three year-old plants grown on their own roots.

Figure 1:
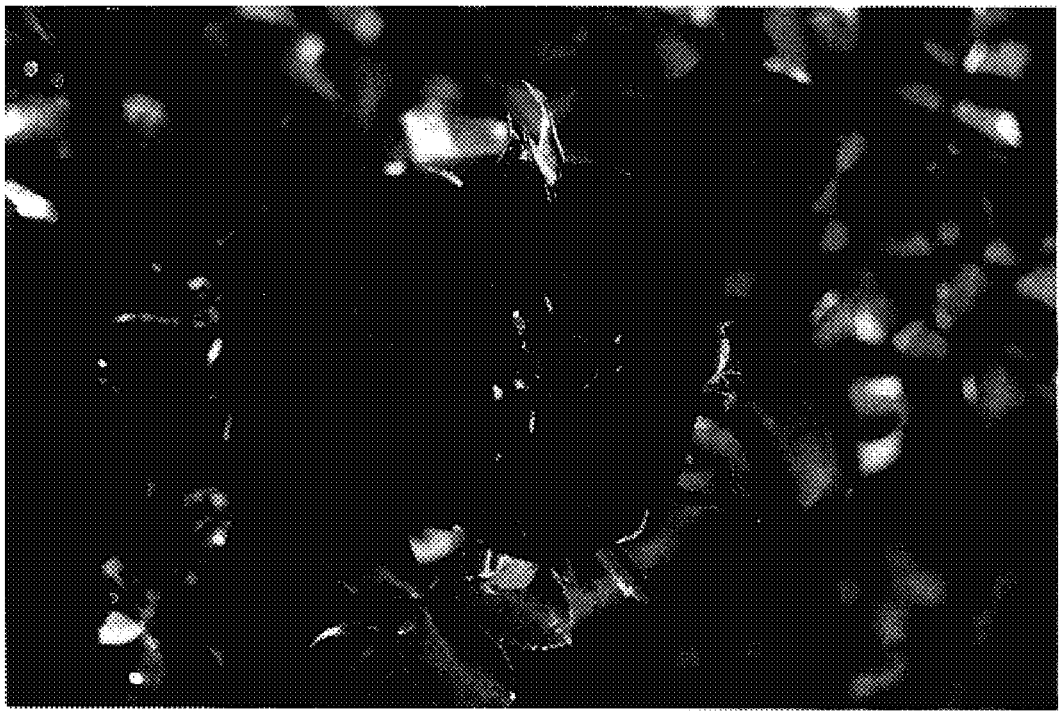
FIG. 1 illustrates a cluster of flowers.
Figure 2:
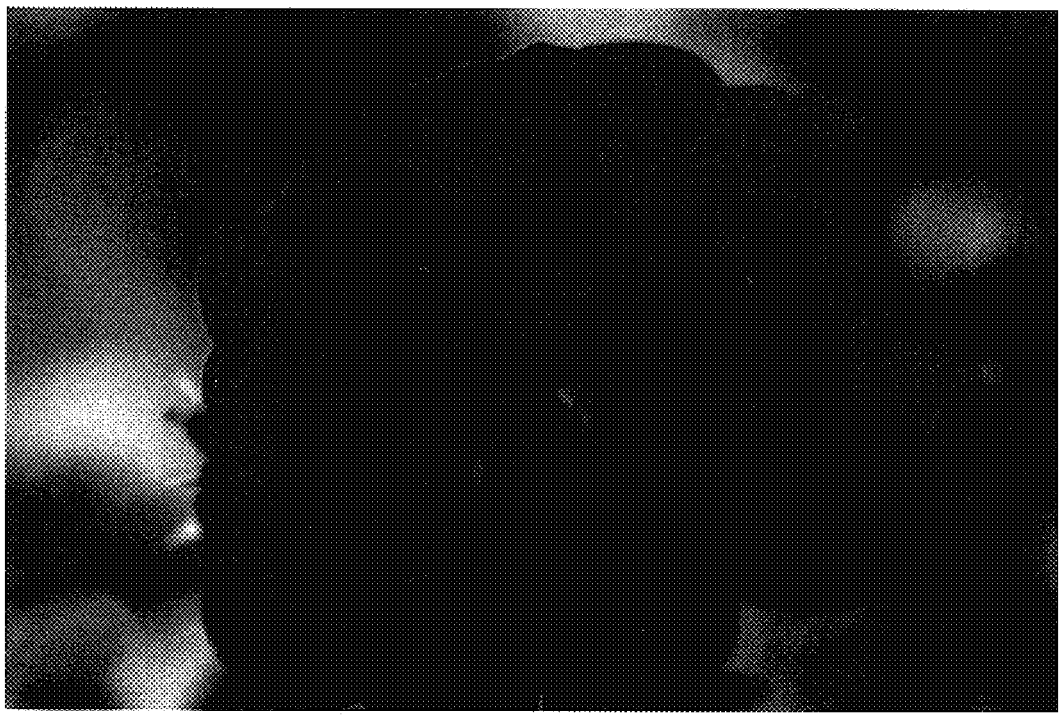
FIG. 2 provides a close-up view of a flower in full bloom.
Figure 3:
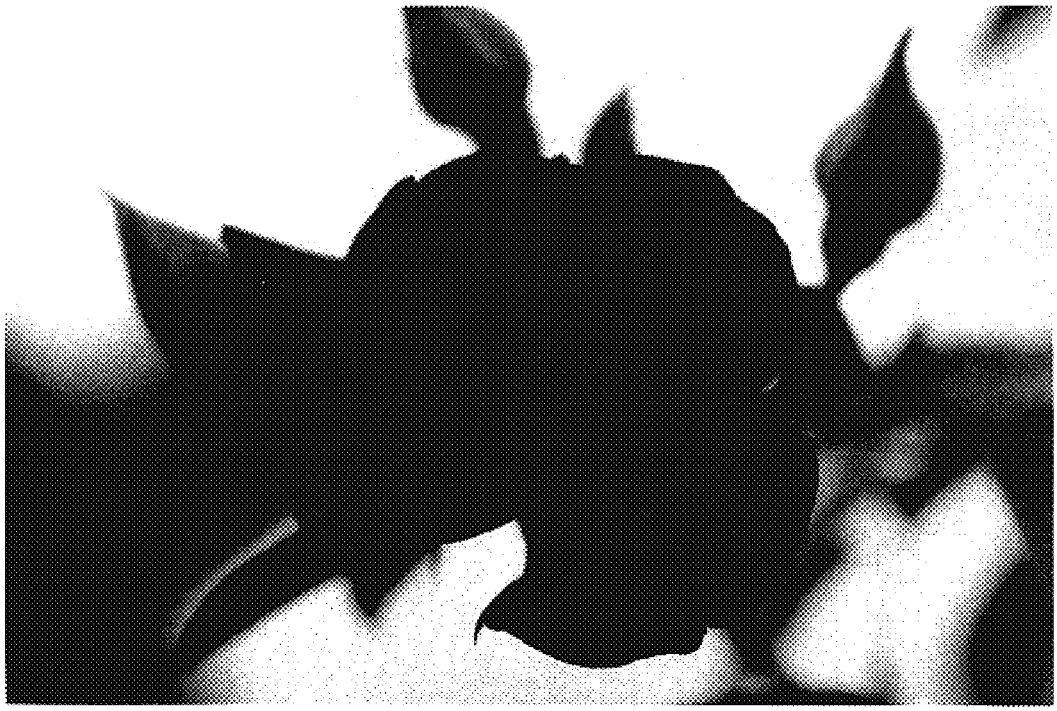
FIG. 3 provides a close-up view of an opening flower and developing flower buds.
Figure 4:
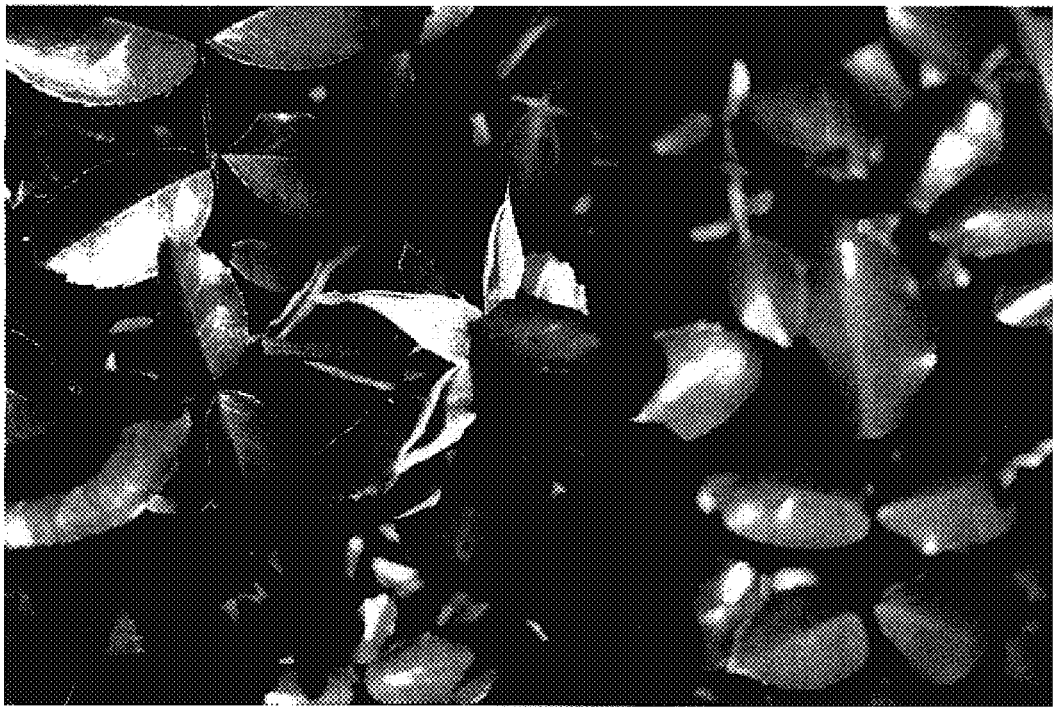
FIG. 4 illustrates the foliage and a flower bud just prior to opening.

The colors in the photographs are as close as possible with digital photography techniques available, the color values cited in the detailed botanical description accurately describe the colors of the new shrub rose.

DETAILED BOTANICAL DESCRIPTION

The following is a detailed description of the new cultivar as observed on two and four year-old plants grown outdoors under field conditions in Yamhill, Oreg. and St. Paul, Minn. The phenotype of the new cultivar may vary with variations in environmental, climatic, and cultural conditions, as it has not been tested under all possible environmental conditions. The color determination is in accordance with The R.H.S. Colour Chart of The Royal Horticultural Society, London, England, except where general color terms of ordinary dictionary significance are used.

General description:

*Botanical classification.*—*Rosa hybrida* 'BAItown'.

*Parentage.*—Seed parent *Rosa* 'KORnuma', pollen parent *Rosa* 'JACcasp'.

*Blooming habit.*—Continuous throughout the season.

*Plant habit.*—Compact, dense, spreading to mounding.

*Height and spread.*—Reaches 60 to 90 cm in height and 60 cm to 1 m in spread.

*Cold hardiness.*—U.S.D.A. Zone 4 to 9.

*Disease and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous and strong.

Branch description:

*Stem color.*—Young; a color between 143A and 143B, maturing; 143A, mature wood; 146B with streaks of 197A.

*Stem surface.*—Young; glabrous with few thorns and prickles, adult wood; mostly glabrous with bark-like ridges.

*Thorns.*—Curved and slightly hooked in shape, canoe to egg-shaped base, average of 9 per 5 cm in number, average of 4.5 mm in length, 182A in color.

Foliage description:

*Leaves.*—Division is odd-pinnate, average of 8.8 cm in length and 5.5 cm in width, internode length is an average of 1.3 cm.

*Leaflets.*—5 or 7 in number (mostly 7), oval to rotund in shape, serrated margins, glabrous and glossy on upper surface, glabrous on lower surface, average of 3.5 cm in length (range 4.0 to 2.8), average of 1.6 cm in width (range 2.0 to 1.3), color: young leaves upper and lower surface; between 187A and 187B with 151 D in region near and on main vein, mature leaves upper surface; between 147A and 147B, mature leaves lower surface; 147B.

*Rachis.*—Average of 3.7 cm in length and 0.9 mm in diameter, color is 143A to 144B with some overlay of 183A with sun exposure.

*Stipules.*—Parallel with auricle facing outward, average of 1.1 cm in length and 5.3 mm in width, upper surface color; auricles 143A, middle 145B, lower surface color; 143A.

*Petioles.*—Average of 1.6 cm in length and 1 mm in diameter, color of upper and lower surface; 143A on edges and 144B in center, glabrous surface.

Inflorescence description:

*Inflorescence type.*—Corymb of double flowers.

*Flower number.*—Average of 3 per lateral stem.

*Flower fragrance.*—Slight apple scent.

*Flower longevity.*—About 5 to 8 days, depending on heat and sunlight exposure.

*Flower type.*—Double, corolla shape is cupped to imbricate with some reflexed outer petals.

*Flower size.*—Average of 8 cm in diameter and 2 cm in depth.

*Peduncles.*—Strong, average of 2.2 cm in length and 3 mm in diameter, color is between 144A and 144B and 183A to 183B on side facing the sun.

*Flower buds.*—High centered and pointed to slender in form, medium in size with an average of 1.9 cm in length and 1.3 cm in width prior to opening, color between 185B and 185C.

*Sepals.*—5, broadly lanceolate in shape, margin is entire with foliaceous appendages in pinnate pattern on the outer and center sepals, color of upper surface 143A, color of lower surface 144A suffused with 185B, upper surface is tomentose, lower surface is strigose, average of 1.9 cm in length and 7.3 mm in width, apex is apiculate changing to a small leaf on the outer and center sepals and acuminate on the inner sepals, base is blunt, aspect is upright in bud stage changing to horizontal when bud opens and reflexed in full bloom.

*Petals.*—Average of 20, drop readily and cleanly, obovate, upper and lower surface is glabrous and satiny, entire margin, rounded base, rounded to emarginate apex, average of 3.6 cm in length and 3 cm in width, color: opening flowers upper surface; 53A, opening flowers lower surface; between 53D and 54A, fully open flowers upper surface; 46A with highlights of 46B and 46C, fully open flowers lower surface; 53C, end of bloom upper surface; darker than 67A suffused with 46A and 46B, end of bloom lower surface; 66D with highlights of 54C and 54D, base petal spot; 4D.

*Receptacle.*—Average of 7.7 mm in diameter and 8.1 mm in depth, urn-shaped, glabrous with some glaucous coating, color is 143B with 183C on the side exposed to sun.

*Pistils.*—Average of 32, stigma is an average of 0.5 mm in length, an average of 0.3 mm in width and 151C in color, style is an average of 4.1 mm in length and 5C in color.

*Stamens.*—Average of 57, filaments are about 5 mm in length and 14A in color, anthers are an average of 2.1 mm in length, an average of 1.1 mm in width and 15B in color, pollen is 19B in color.

*Hips.*—None have formed under the trial conditions.

We claim:

1. A new and distinct cultivar of shrub rose plant named *Rosa* 'BAItown' as herein illustrated and described.

* * * * *